United States Patent
Mohamed et al.

(10) Patent No.: US 10,989,711 B1
(45) Date of Patent: Apr. 27, 2021

(54) GOLD@ZINC SALEN-BASED METAL ORGANIC FRAMEWORK COMPOSITE AND METHODS OF USE THEREOF

(71) Applicant: King Abdulaziz University, Jeddah (SA)

(72) Inventors: Reda Mohamedy Mohamed, Jeddah (SA); Mohammad W. Kadi, Jeddah (SA); Said M. El-Sheikh, Jeddah (SA); Sheta M. Sheta, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/104,008

(22) Filed: Nov. 25, 2020

(51) Int. Cl.
*G01N 33/547* (2006.01)
*G01N 33/549* (2006.01)
*G01N 33/566* (2006.01)
*G01N 33/543* (2006.01)
*G01N 33/68* (2006.01)

(52) U.S. Cl.
CPC ..... *G01N 33/54353* (2013.01); *G01N 33/689* (2013.01); *G01N 2333/726* (2013.01)

(58) Field of Classification Search
CPC .......... G01N 33/54353; G01N 33/689; G01N 2333/726
See application file for complete search history.

(56) References Cited

PUBLICATIONS

Yuan et al. Metallosalen-based crystalline porous materials: synthesis and property. Coordination Chemistry Reviews 2019, vol. 378, pp. 483-499. (Year: 2019).*

Yuan et al. Gold nanoparticle-decorated metal organic frameworks on immunochromatographic assay for human chorionic gonadotropin detection. Microchim Acta 2020, vol. 187, No. 640, pp. 1-9. (Year: 2020).*

Kleij, Arjan. Zinc-centred salen complexes: versatile and accessible supramalecular building motifs. Dalton Trans 2009, pp. 4635-4639. (Year: 2009).*

Raisanen et al. Cobaltsalen functionalised polycrystalline gold surfaces. Thin Solid Films 2008, pp. 2948-2956. (Year: 2008).*

Dhakshinamoorthy et al. Gold-nanoparticle-decorated metal-organic frameworks for anticancer therapy. ChemMedChem 2020, vol. 15., pp. 2236-2256. (Year: 2020).*

Bahrani et al., "Zinc-based metal—organic frameworks as nontoxic and biodegradable platforms for biomedical applications: review study" (2019), Drug Metabolism Reviews.

Guo et al., "Natural enzyme-free colorimetric immunoassay for human chorionic gonadotropin detection based on the Ag+-triggered catalytic activity of cetyltrimethylammonium bromide-coated gold nanoparticles", Sensors and Actuators B: Chemical, Colume 305, Feb. 15, 2020, 127439.

Sheta et al., "A novel, fast, high sensitivity biosensor for supporting therapeutic decisions and onset actions for chest pain cases", RSC Adv., 2019, 9, 20463.

(Continued)

*Primary Examiner* — Shafiqul Haq
(74) *Attorney, Agent, or Firm* — W & C IP

(57) ABSTRACT

A metal organic framework composite is provided. The composite includes a plurality of zinc ions, each coordinated with a salen ligand to form a salen complex metal-organic framework; and gold nanoparticles dispersed on a surface and pores of the salen complex metal-organic framework. Antibodies may be immobilized on a surface of the gold nanoparticles to be used in highly sensitive diagnostic methods for detecting and quantifying protein biomarkers such as human chorionic gonadotropin hormone.

13 Claims, 10 Drawing Sheets

(56) References Cited

PUBLICATIONS

Yadav et al., "Gold Nanoparticles Incorporated in a Zinc-Based Metal-Organic Framework as Multifunctional Catalyst for the Oxygen Reduction and Hydrogen Evolution Reactions", ChemElectroChem, vol. 5, Issue 18, Jun. 29, 2018.

Yuan et al., "Metallosalen-based crystalline porous materials: Synthesis and property", Coordination Chemistry Reviews, (2017).

Yuan et al., "Gold nanoparticle-decorated metal organic frameworks on immunochromatographic assay for human chorionic gonadotropin detection", Nov. 5, 2020, Microchimica Acta 187, Article 640.

* cited by examiner

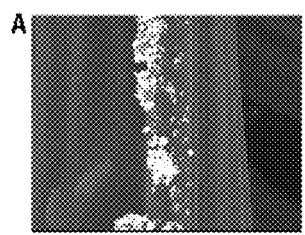 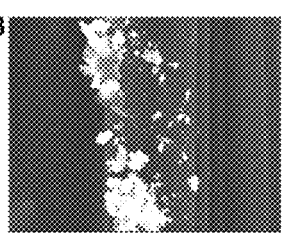 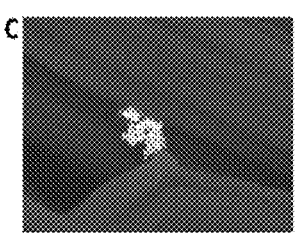 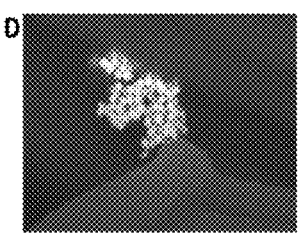
FIG. 3A  FIG. 3B  FIG. 3C  FIG. 3D
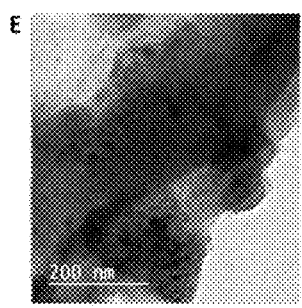 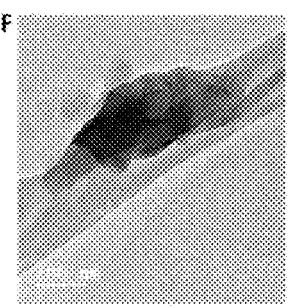 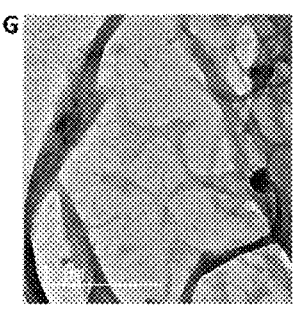 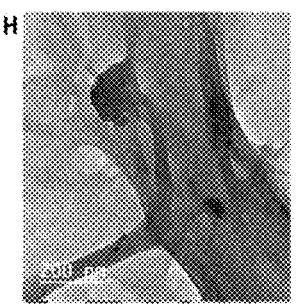
FIG. 3E  FIG. 3F  FIG. 3G  FIG. 3H

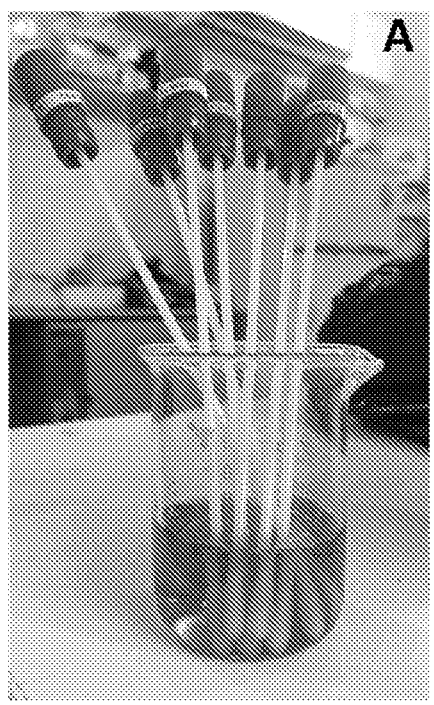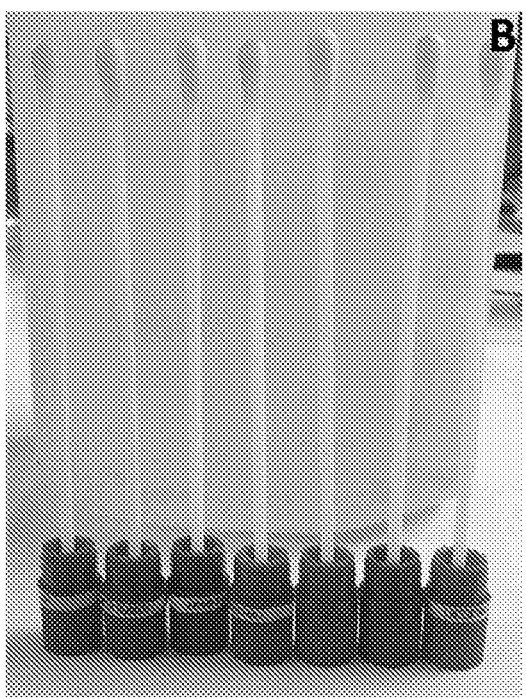
FIG. 5A  FIG. 5B
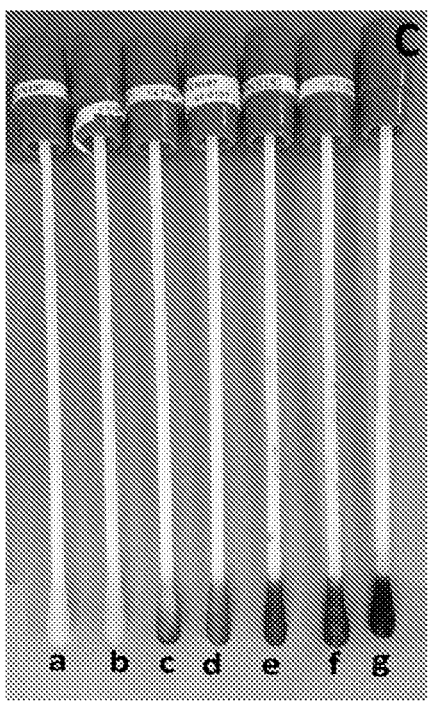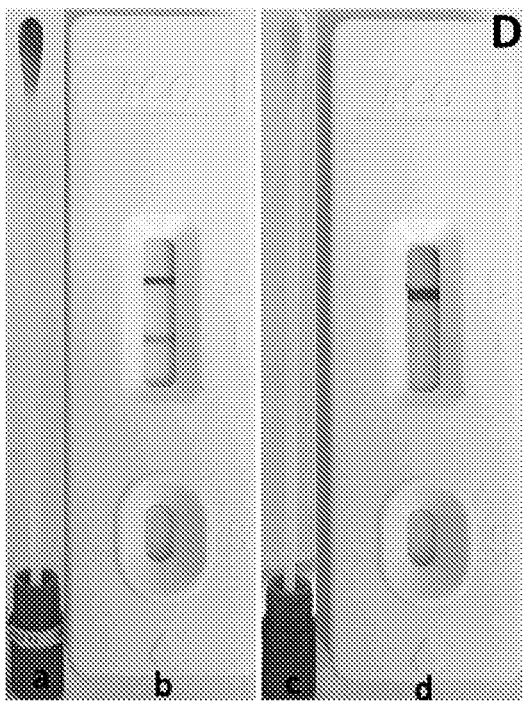
FIG. 5C  FIG. 5D

Zn(NO$_3$)$_2$.6H$_2$O
(2.0 mmol)

+

Organic nano-linker           Reflux at 100 °C for 48 h
(1.0 mmol)          ─────────────────────────────→   Au@Zn-Salen MOF composite
                    1- Reduction of Au with DMF/Ethanol.
+                   2- Formation of Zn-Salen MOF
                    3- Incorporation of Au at Zn-Salen MOF HAuCl$_4$.3H$_2$O
(2.0 mmol)

FIG. 9

GOLD@ZINC SALEN-BASED METAL ORGANIC FRAMEWORK COMPOSITE AND METHODS OF USE THEREOF

FIELD OF THE INVENTION

The invention is generally related to gold@ zinc salen-based metal organic framework composites that may be utilized in highly sensitive and selective methods for detecting and quantifying protein biomarkers.

BACKGROUND OF THE INVENTION

Early detection of diseases and tumor biomarkers are very important for disease screening and development of treatment strategies. However, many medical laboratories' diagnostic tests are time-consuming, require several steps of sample preparation, and require infra-construction instruments and a well-trained staff [1]. Point of care testing (POCT) allows patients and clinicians to make initial fast decisions especially in resource-limited countries. The market size for self-testing devices and POCT devices has grown by about 10% in the last decade [2].

Generally, qualitative and quantitative tests for human chorionic gonadotropin (hCG) hormone are commonly performed to determine the status of a woman's pregnancy [6]. However, hCG has many biological functions and biochemical properties with clinical applications beyond the determination of pregnancy status. The concentration of hCG is elevated in cases of trophoblastic placental tumors for women and also elevated in about twenty to forty percent of seminomas in men [9]. High concentrations of hCG in non-pregnant women are an indication of diseases such as tumors of the ovaries, pancreas, bladder, lungs, stomach, and liver [10]. The hCG hormone can be used in diagnosis of gestational trophoblastic disease, testicular germ cell tumors (testicular cancers), ectopic pregnancy, and different tumor neoplasms. The hormone may also be used in combination with other biomarkers for the screening of fetal aneuploidies cases [3, 11].

Thus, accurate, precise, and sensitive determination of hCG hormone in plasma, serum, or urine samples is an important research point for continuous development. Up to date, various analytical methods, technologies, and devices have been reported for the detection of hCG such as lateral flow assay [14, 15], HILIC-MS [16], electrochemiluminescence immunoassay [3, 7], voltametric immunosensor [17], chemiluminescence lateral flow immunoassay [18], colorimetric immunoassay [4, 19, 20], luminescence assay [21], nanosheet array-based immunosensor [22], and fluorescence method [23]. Each of the aforementioned methods or techniques have merits and advantages, but at the same time, have certain limitations and defects.

A colloidal-gold immune-chromatography method is one of a common, rapid, low cost test used for detection and on-site screening of various biomarkers [15]. This method joined the features of chromatography and immunoassay technologies [24, 25]. The immobilization of antibodies and the amplification of signals is the key component in the manufacture and development of these types of immunosensors.

On the other hand, metal organic frameworks (MOFs) are an attractive category of crystalline heterogeneous highly porous materials having pores and channels with a specific size that allows for the capture of small molecules and gases as an example. Classically, MOFs comprise inorganic nodes (metal nodes or clusters) that are bonded by organic linkers via non-covalent and covalent bonding [26-30]. The topologies, morphologies and surface functionality (simple functionalization) of these materials can readily be controlled and tuned by changing the constituent metals, clusters, and/or types of organic ligand or linkers used [31]. MOFs have been developed as functional materials for encapsulating or embedding nanoparticles of noble metals such as Au and Pt [32, 33]. Salen based MOFs have also been developed [34-39], e.g. multi-metallic-salen-frameworks in which the metal-host forms adducting complexes with additional structural ordering based on the substrate binding [40-43]. MOFs have attracted a great attention, owing to versatile skeleton design, tunable pore size, large surface area, and high thermal and chemical stability [44-51].

Novel MOFs that can be incorporated into more efficient diagnostic methods are needed.

SUMMARY

Described herein are gold @ zinc salen based MOF (Au@Zn-SMOF) composite which may be prepared via a simple in-situ reaction. The Au@Zn-SMOF composite may be used as a biosensor for detection and quantification of various protein biomarkers such as hCG at ultra-low concentration levels.

An aspect of the disclosure provides a metal organic framework composite, comprising a plurality of zinc ions, each coordinated with a salen ligand to form a salen complex metal-organic framework; and gold nanoparticles dispersed on a surface and in pores of the salen complex metal organic framework. In some embodiments, the salen ligand is as shown in FIG. 8. In some embodiments, the salen complex metal organic framework forms nanosheets. In some embodiments, the nanosheets have a thickness of 100 nm or less. In some embodiments, the gold nanoparticles have a diameter of 350-450 nm. In some embodiments, the composite further comprises an antibody immobilized on a surface of the gold nanoparticles. In some embodiments, the antibody is a β-human chorionic gonadotropin (hCG) monoclonal antibody.

Another aspect of the disclosure provides a device for detecting a protein biomarker in a biological sample, comprising a metal organic framework composite as described herein arranged on a substrate. In some embodiments, the substrate is a cotton swab.

Another aspect of the disclosure provides a method of detecting a protein biomarker in a biological sample, comprising contacting the biological sample with a metal organic framework composite as described herein under conditions suitable for binding the protein biomarker; and detecting the protein biomarker by observing a colorimetric change in the solution. In some embodiments, the biological sample is selected from the group consisting of serum, plasma, and urine. In some embodiments, the colorimetric change is from yellow to green.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 3A-H. (A-D) Field-emission scanning electron microscopy images (FE-SEM) of the Au@Zn-SMOF@Ab on the surface of a swab at different magnifications. (E-H) Transmission electron microscopy images (TEM) of the Au@Zn-SMOF@Ab on the surface of swab fibers at different magnifications (E) without hCG hormone, and (F-H) with hCG hormone.

FIGS. 5A-D. A smartphone photography images for swab test device preparation and optimization: (A) A sterile cotton swab (CITOAWAB) soaked in a beaker containing Au@Zn-SMOF@Ab, (B) Ready to use swab device, (C) Swab device optimization against different concentrations of β-hCG hormone standard [a, Control; b, 5.0 mIU/mL; c, 20.0 mIU/mL; d, 50.0 mIU/mL; e, 100.0 mIU/mL; f, 500.0 mIU/mL; and g, 1000.0 mIU/mL], and (D) A comparison between the swab test device and a pregnancy cassette on the market [a, b Positive pregnant case; c, d Negative pregnant case].

FIG. 9. A reaction mechanism scheme of the Au@Zn-SMOF composite synthesis according to some embodiments of the disclosure.

DETAILED DESCRIPTION

Embodiments of the disclosure provide gold @ zinc salen based metal organic framework (Au@Zn-SMOF) composite useful as highly sensitive and selective biosensors.

As used herein, the term "metal organic framework" refers to a crystal compound having a periodic network structure, formed by self-assembly of oxygen-containing polydentate organic ligands and metal ions. The composite of the present disclosure comprises a plurality of zinc ions, each coordinated with a salen ligand to form a salen complex metal organic framework.

Figure 8:
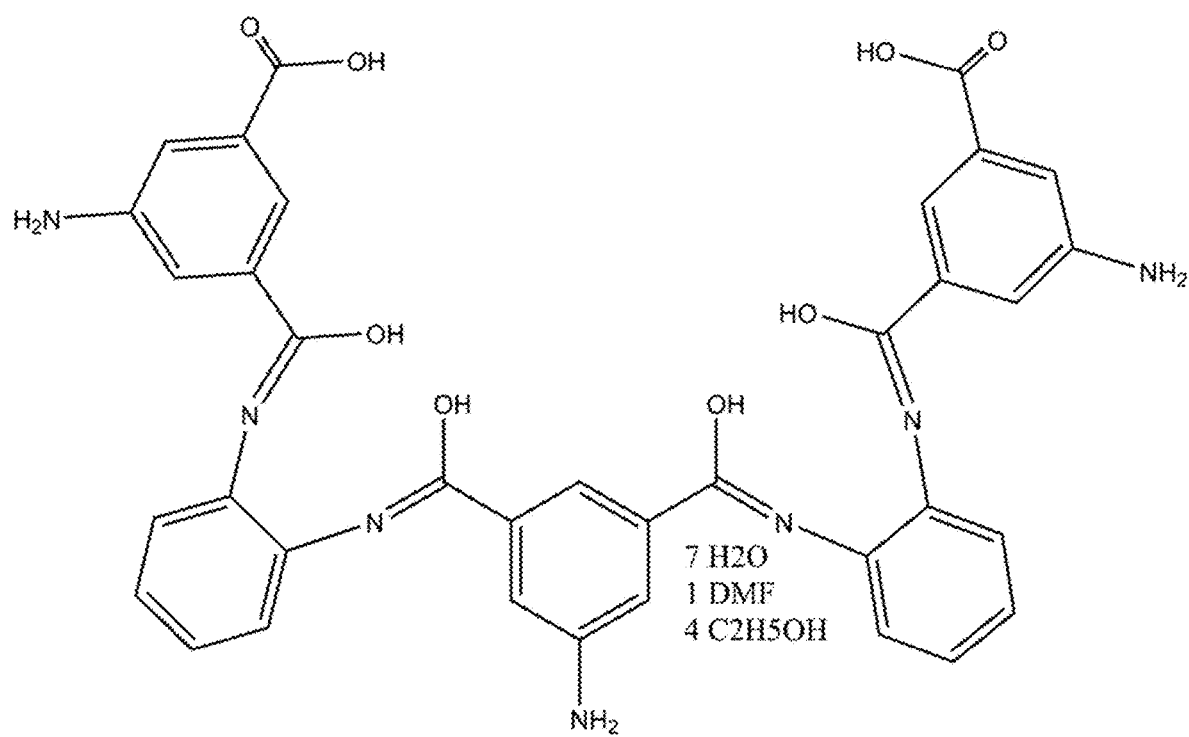
FIG. 8. Chemical structure of an organic nanolinker according to some embodiments of the disclosure.

As used herein, the term "salen ligand" refers to a tetradentate $C_2$-symmetric ligand synthesized from salicylaldehyde (sal) and ethylenediamine (en). Salen ligands may coordinate a wide range of different metals, which they can often stabilize in various oxidation states. In some embodiments, the salen ligand is an organic nanolinker formed by reacting 5-aminoisophthalic acid and 1,2-phenylenediamine (FIG. 8). Other suitable salen ligands include, but are not limited to, pyridine functionalized Salen-metal complex with tetrakis(4-carboxyphenyl)benzene, dicarboxalic acid linkage, and pyrrole based salen type ligand.

In some embodiments, the salen complex metal organic framework forms nanosheets. As used herein, the term "nanosheets" refers to a two-dimensional nano material having its lateral dimensions larger than its thickness. In some embodiments, the nanosheets have a thickness of about 1-100 nanometers, e.g. a thickness of about 100 nm or less.

A composite as described herein comprises gold nanoparticles dispersed on a surface and pores of the salen complex metal organic framework. In some embodiments, the gold nanoparticles are generally spherical and have a diameter of about 300-500 nm, e.g. 350-450 nm.

In some embodiments, the composite further comprises an antibody immobilized on a surface of the gold nanoparticles. The antibody may be immobilized using methods known in the art such as electrostatic adsorption. For use as a biosensor, any type of monoclonal or polyclonal antibody may be associated with the composite depending on the biomarker for which detection/quantification is desired. For example, a β-human chorionic gonadotropin (hCG) monoclonal antibody may be used to detect hCG hormone in biological samples. Other antibodies that may be incorporated include antibodies that bind to protein biomarkers such as alpha-fetoprotein (AFP) (as an indication of neural tube defects), cardiac troponin I (cTnI) (to monitor acute myocardial infarction in patients), alpha-II Spectrin Breakdown Product (SBDP) (to diagnose traumatic brain injury), carcinoembryonic antigen (CEA) for colon and rectal cancers, cancer antigen 125 (CA125) for ovarian cancer, Prostate-Specific Antigen/Kallikrein 3 (PSA/K3) for prostate cancer, and Human Epidermal growth factor Receptor 2 (HER2/Neu) for breast cancer.

Human chorionic gonadotropin hormone, is a 37000 Dalton multi-functional heterodimeric glycoprotein polypeptide hormone, produced by trophoblast cells which form the placenta during pregnancy and is elevated in trophoblast and non-fibroblast tumors [3-5]. It mainly consists of two subunits (α-hCG and β-hCG), but has a large number of glycol-forms because of its eight sites of potential glycosylation. Rapid hCG tests for urine or serum samples can be performed as a POCT via qualitative tests, whereas quantitative hCG tests in serum are usually performed in a medical laboratory. For the quantitative assay, an hCG concentration below 5.0 mIU/mL is indicative of a nonpregnant female (negative pregnancy), values between 5.0-20.0 mIU/mL are equivocal titer, and values more than 25.0 mIU/mL are indicative of a positive pregnancy [2, 7, 8]. During pregnancy, hCG hormone promotes uterine angiogenesis to guarantee a high blood quantity is provided to the invading placenta [12]. hCG is also a cancer promoter in all malignancies of human and is an enhancement to pituitary luteinizing hormone during the menstrual-cycle [13].

The ability to quantitate the β-hCG level is useful in monitoring germ cell and trophoblastic tumors, follow-up care after miscarriage, and diagnosis of and follow-up care after treatment of ectopic pregnancy. Human chorionic gonadotropin can also be used as a tumor marker, as its β subunit is secreted by some cancers including seminoma, choriocarcinoma, germ cell tumors, hydatidiform mole, teratoma with elements of choriocarcinoma, and islet cell tumor. For this reason, a positive result in males can be a test for testicular cancer. The normal range for men is between 0-5 mIU/mL, with higher levels being indicative of cancer. hCG levels may also be used to diagnose ovarian, stomach, and liver cancer among others.

Thus, some embodiments of the disclosure provide a device for detecting a biomarker (e.g. hCG) in a biological sample, comprising a metal organic framework composite with an immobilized antibody as described herein arranged on a substrate. In some embodiments, the substrate is any suitable absorbent substrate such as a cotton swab, cloth, or sponge material. In some embodiments, the substrate was previously soaked in a solution (e.g. a phosphate buffer solution) containing the metal organic framework composite and then dried.

The device may be used in methods of detecting and/or quantifying biomarkers in a biological sample. Suitable biological samples include, but are not limited to, serum, plasma, whole blood, urine, stool, saliva, amniotic fluid, cerebrospinal fluid, tissue, transcervical lavage fluid, etc.

The device described herein may be provided as part of a kit which includes a means for sample collection and a means for contacting the substrate with the sample. Suitable materials for such kits are known in the art, e.g. materials provided in over-the-counter pregnancy test kits.

Detection methods as described herein include steps of contacting the biological sample with a metal organic framework composite having an associated antibody as described herein under conditions suitable for binding the biomarker, e.g. hCG and detecting the biomarker by observing a colorimetric change in the solution. Suitable conditions may include, for example, submerging the substrate in the biological sample for a suitable length of time that allows binding of the antibody to the biomarker, in 1 minute or less. Binding typically occurs at room temperature. In some embodiments, the colorimetric change is from yellow to green in about 10 minutes or less. In some embodiments, the quantitation can be performed using reflective spectroscopy to monitor the absorbance/color intensity at different wavelengths. The absorbance of the green color produced in the assay falls in the range of about 495 nm to about 570 nm while the absorbance of the yellow color is in the range of about 570-590 nm. The biosensing platform is based on a high specific antigen/antibody immune recognition response. When the protein biomarker is bound by the antibody, the color changes via formation of a sandwich complex structure from yellow to green.

Embodiments of the disclosure also provide methods of preparing a composite as described herein. For example, the composite may be prepared by reacting the organic nano linker with an equal molar ratio of $Zn(NO_3)_2 \cdot 6H_2O$ and $HAuCl_4 \cdot 3H_2O$. In this reaction the mechanism takes place in two steps, by forming adduct complex Zn(II) ions are situated in the center of the nano-linker forming the helical complex followed by further ordering of the structure via substrate binding with gold ions on the outer node of the complex forming Au @Zn-SMOF composite.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Human chorionic gonadotropin (hCG) hormone is not only used to determine pregnancy status but it is also a biomarker that plays a vital and autocrine role in the promotion of tumor growth, human cancer biology, invasion, and malignant tumors (as an example, tumors of ovaries, stomach, and liver). Development of sensitive qualitative/quantitative methods and innovative novel efficient devices for the detection of hCG as a biomarker for tumor and early pregnancy prediction remains a challenge. In this work, a novel gold@zinc salen metal-organic framework composite (Au @Zn-SMOF) was prepared via novel in-situ simple reaction of organic nano-linker with Zn $(NO_3)_2.6H_2O$ and $HAuCl_4.3H_2O$. The synthesized Au@Zn-SMOF composite was characterized by various micro-analytical and spectral tools. A novel swab test device and simple colorimetric method for hCG hormone detection based on Au@Zn-SMOF composite is provided. The swab test device (qualitative method) comprises a simple cotton swab soaked in a solution of Au@Zn-SMOF composite with hCG antibodies (hCG-Ab) immobilized therein. Au@Zn-SMOF composite was worked as a nanozyme to authenticate a natural enzyme-free immunoassay. When the cotton swab contacts serum-plasma or urine patient samples, the color changes from yellow to different degrees of green based on the concentration of hCG hormone in the sample. Through that, a visual indication of positive or negative pregnancy result is provided. This device can be used to detect pregnancy at the early stages or be used as an indication for elevated hCG concentration as a tumor biomarker. This device can easily transfer to commercially costless kits (lower cost about 25-30%-fold than in the market) and can be used at home in terms of near-patient testing (applications of the point-of-care testing (POCT)). For the quantitative colorimetric method, under optimal conditions, the biosensor exhibits a fast-stable response for hCG in a range between (0.001-3000 mIU/mL) with a detection limit of 0.055 mIU/mL and quantification limit of 0.167 mIU/mL. The developed colorimetric biosensor exhibited high selectivity towards hCG over the competing matrix.

Materials and Methods

Synthesis of the Gold@Zinc Salen-MOF Composite

A Au@Zn-SMOF composite was prepared via in-situ simple reaction of equal molar ratio of $Zn(NO_3)_2.6H_2O$ (2.0 mmol, 0.595 g) and $HAuCl_4.3H_2O$ (2.0 mmol, 0.788 g) both dissolved in 10 ml distilled water (DW) and was added dropwise to a round flask containing organic nano-linker (1.0 mmol) (FIG. 8) which was prepared by Sheta et al., [52]. This system was stirred and refluxed at 100° C. for 48 h. A produced light green-brown precipitate was filtered, washed, and left to thoroughly dry at room temperature. The reaction scheme is represented in FIG. 9.

Swab Test Device Biosensing Platform Preparation and Optimization

In this step, the β-hCG hormone antibodies (β-hCG-Ab) were immobilized on the surface of Au@Zn-SMOF composite via classic-electrostatic adsorption to form Au@Zn-SMOF@Ab according to references [15, 20, 53-55] with some modifications. A 10 µM of Au@Zn-SMOF composite was suspended in 50 mL of phosphate buffer solution (PBS) at pH 7.4. Then, 2.5 mM of anti-β-hCG-Ab was added dropwise into the Au@Zn-SMOF composite solution. The Au@Zn-SMOF@Ab solution was incubated with a gentle magnetic stirring for 1 hour. After that, 25.0 mL 1% (w/v) of bovine serum albumin (BSA) was added and the system was incubated for another 1 hour to block the uncovered open site on the surface of Au@Zn-SMOF composite. To use for the detection probe/biosensing platform (Au@Zn-SMOF@Ab), the above mixture was centrifuged and then resuspended in 2.5 mL of solution containing of (PEG 20000 1%, fructose 2%, sucrose 5%, BSA 1%, Tween-20 0.4% and trisodium citrate 0.2%) and kept ready for use. Sterile cotton swabs (CITOAWAB) from a local market were soaked in a beaker containing 25 mL Au@Zn-SMOF@Ab overnight, then left to dry at room temperature. After drying, the swabs were tested in different concentrations of hCG hormone standard as well as real samples.

General Procedures for Colorimetric Determination Method of hCG Hormone

A working solution (10 µM) of Au@Zn-SMOF composite was prepared from the stock solution (100 µM dissolved in DMSO) by diluting with PBS. Then the immobilization was carried out in solution via classic-electrostatic conjugation to form Au@Zn-SMOF@Ab. The Au@Zn-SMOF@Ab solution was subjected to UV-vis absorption measurements then against a freshly prepared series concentration of hCG hormone in buffered solution. Upon optimization of the absorption measurement conditions, a linear relationship was found between the Abs intensities of Au@Zn-SMOF@Ab and series concentration of hCG hormone in a range between 0.001-3000 mIU/mL, and according to linear-relationship equation: Y=a+bX "In which; Y, is the absorption intensities of the Au@Zn-SMOF@Ab; a and b are the intercept and slope of the linear-relationship, respectively; and X, is the hCG hormone concentrations". The LOD and LOQ were estimated from the equations: "LOD= (S/b)*3.3 & LOQ=(S/b)*10 [56-58]. Where S and b are the standard errors of absorption intensities; and the slope of the linear relationship, respectively". Moreover, the Au@Zn-SMOF@Ab solutions were subjected to absorption measurements against different interfering matrix in a separate cell and a mixture with hCG hormone to performed the selectivity study.

Quantification of hCG Hormone in Real Samples

The real serum, plasma and urine samples were supplied from a medical lab. The samples were handled and pre-treated according to the standard precautionary guidelines to avoid possible infectious material and subject to measurements as described in the above sections.

Results and Discussion

Au@Zn-SMOF Composite, Au@Zn-SMOF@Ab, and Au@Zn-SMOF@Ab@h-CG Characterization

Au@Zn-SMOF composite was prepared via in-situ simple reaction organic nano-linker (FIG. 8) with equal molar ratio of $Zn(NO_3)_2.6H_2O$, and $HAuCl_4.3H_2O$ according to reaction Scheme (FIG. 9). A light green-brown precipitate resulted from the reaction was filtered, washed, and left to thoroughly dry. In this reaction, the mechanism takes place in three steps as follows: (i) The first step, reduction of Au with DMF/Ethanol [59-61]. DMF is used as a reducing agent in the chemical wet synthesis of metallic nanoparticles. DMF has been used as a reducing agent for $Ag^+$[62, 63], $Ni^{2+}/Co^{2+}$[64], $Cu^{2+}$[65], $Pd^{2+}$[66], and $Au^{3+}$ [67, 68] ions, to produce the corresponding metal nanoparticles at convenient temperatures according to the equation (1).

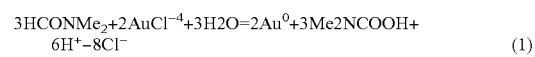

$$3HCONMe_2 + 2AuCl^{-4} + 3H2O = 2Au^0 + 3Me2NCOOH + 6H^+ - 8Cl^- \quad (1)$$

(ii) In the second and third steps, Zn-Salen MOF were formed and Au was incorporated at Zn-Salen MOF by forming an adduct complex. Zn(II) ions are situated in the center of nano-linker forming the helical complex followed by further ordering of the structure via substrate binding with gold ions on the outer node of the complex forming Au@Zn-SMOF composite. The reaction precipitate yield was 66.3%. In detail, the elucidation of the structure using various quantitative and qualitative microanalytical tools is discussed as follows:

FE-SEM-EDX and TEM Spectroscopy

Figure 1A:
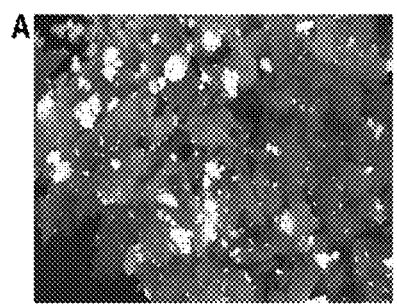
FIGS. 1A-F. (A-E) Field-emission scanning electron microscopy images (FE-SEM) of the Au@Zn-SMOF composite at different magnifications, (F) Energy-dispersive X-ray analysis with a single point EDX mapping analysis of Au@Zn-SMOF composite at different points.
Figure 1B:
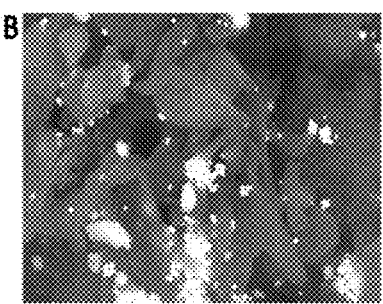
Figure 1C:
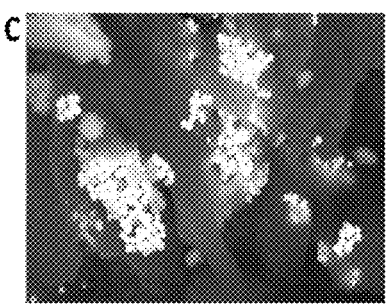
Figure 1D:
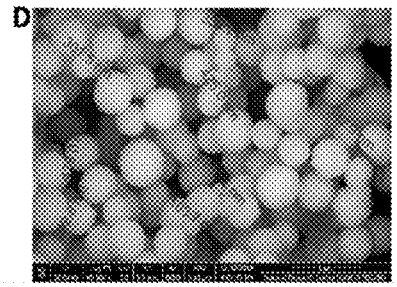
Figure 1E:
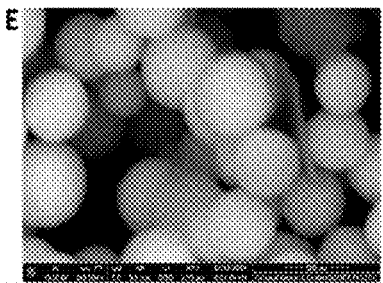

The FE-SEM images revealed the typical morphological features of Au @Zn-SMOF composite (FIG. 1A-E). The characteristic nano-spherical smooth surface morphology of Au and Zn-SMOF with the geometry confining into the layer of nanosheets are obviously observed as shown in FIG. 1A-C. The enlarged FE-SEM image (FIG. 1D, E) shows that the Au nano-spherical morphology are highly monodispersed aggregates in the matrix and the diameter was about 350-450 nm. Whereas the of the Zn-SMOF nanosheets thickness are less than 100 nm.

Figure 1F:
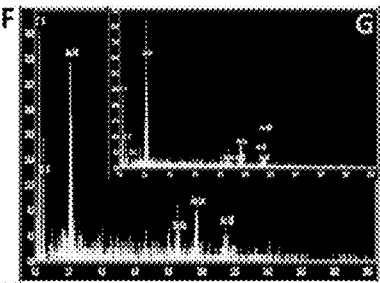

Moreover, the EDX mapping analysis (FIG. 1F, G-(insert-in F)) of Au@Zn-SMOF composite shows the presence of Zn, Au, carbon, nitrogen, and oxygen as a construction element. The outstanding dispersion of the above MOF-elements alongside the cross-section revealed by mapping EDX analysis (FIG. 1F, G) also confirmed the Au@Zn-SMOF composite formation.

Figure 2A:
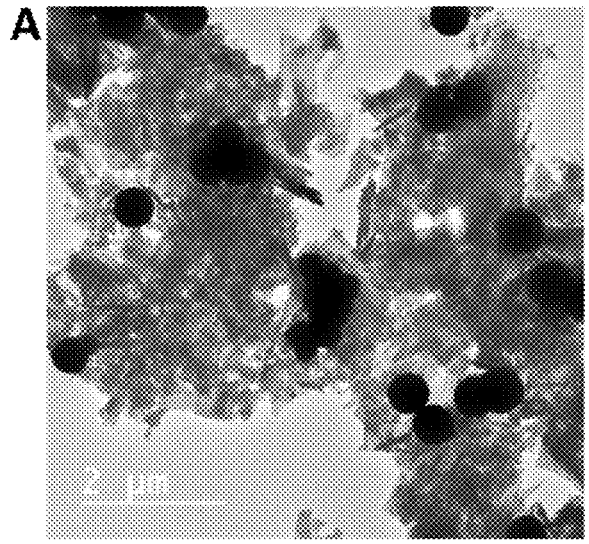
FIGS. 2A-D. (A-C) Transmission electron microscopy images (TEM) of the Au @Zn-SMOF composite at different magnifications. (D) The diffraction pattern (Selected area diffraction) of the Au@Zn-SMOF composite.
Figure 2B:
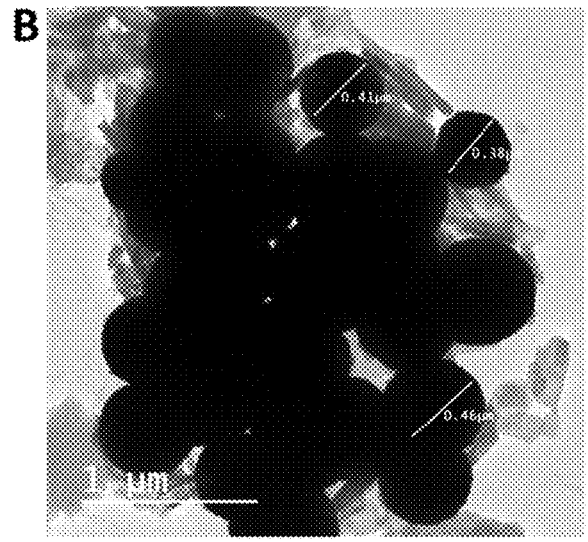
Figure 2C:
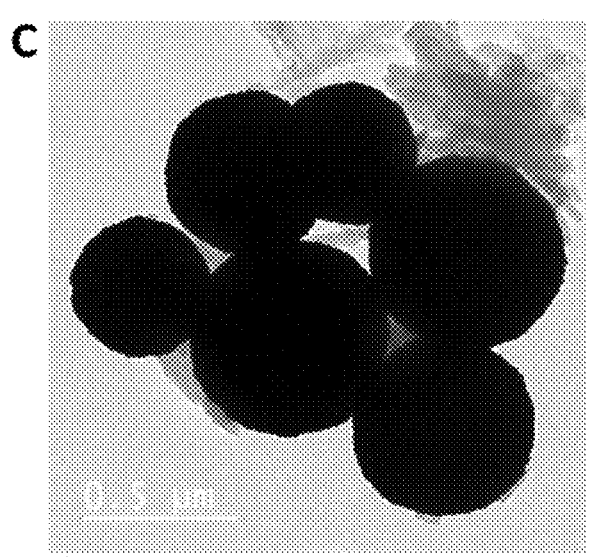
Figure 2D:
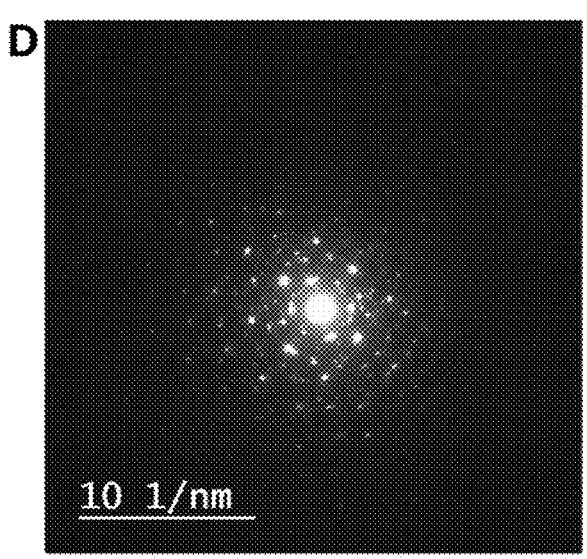

TEM images of Au@Zn-SMOF composite are shown in FIG. 2A-C. From these results, the contrast of Au nanoparticles can be observed more deeply. The morphology of the Au is uniform spherical and the size of spherical nanoparticles is about 350-450 nm which in good agreement with FE-SEM. In addition, the Zn-SMOF small nanosheets are clearly obtained. The selected area diffraction pattern (FIG. 2D) of a single spherical particle confirmed the crystalline nature of gold nanoparticles, the rings assigned (111), (200) and (220) planes of FCC crystalline lattices of gold and polycrystalline nature of Zn-SMOF nanosheets.

FIG. 3(A-D) shows FE-SEM images of the Au@Zn-SMOF composite on the surface of the swab at different magnifications. From these images, a good distribution of Au@Zn-SMOF composite on the surface of swab can be observed (FIG. 3A, B). Whereas, FIG. 3C, D revealed the good connection and linkage between Au and swab. FIG. 3E-H represents the TEM images of the Au@Zn-SMOF@Ab on the surface of swab fibers at different magnifications (FIG. 3E-F) without hCG hormone, and (FIG. 3G-H) with hCG hormone. FIG. 3E-F shows the presence of nanosheets of Au@Zn-SMOF composite over the surface of the swab. On the other hand, FIG. 3G-H revealed different magnifications of the network of Ab between Au nanoparticles, Zn-SMOF nanosheets and swab which confirm the good adhesion on the surface of the swab.

UV-Vis Spectra

The Au@Zn-SMOF composite electronic reflection and bandgap spectra contrasted with organic linker were represented in (FIG. 3A, B), respectively. From (FIG. 3A) the Au@Zn-SMOF composite displays four reflection peaks at 228, 278, 373, and 626 nm with significant blueshift comparing with organic linker. In addition, the values of energy bandgap of Au@Zn-SMOF composite were decreased (1.60 and 1.75 eV) comparing with organic linker energy bandgap values resulting from the high conjugation of the organic linker due to the increasing of the HOMO valance band energy as shown in (FIG. 3B). Moreover, a broad absorption band centered at 465 nm was noticed which was assigned to the surface-plasmon-resonance of the gold nanoparticles [32].

FT-IR

Figure 4A:
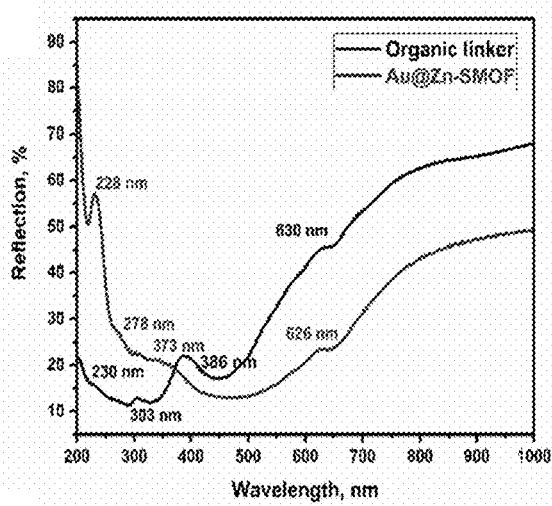
FIGS. 4A-F. (A) The electronic reflection spectra of organic linker and Au @Zn-SMOF composite, (B) The bandgap energy of organic linker and Au@Zn-SMOF composite, (C) The FT-IR spectrum of the Au@Zn-SMOF composite, (D)$^1$H-NMR of the Au@Zn-SMOF composite, (E) The X-ray diffraction spectra of the Au@Zn-SMOF composite, and some references for comparison and (F) The thermogravimetric analysis (TGA-DTA) of the Au@Zn-SMOF composite.
Figure 4B:
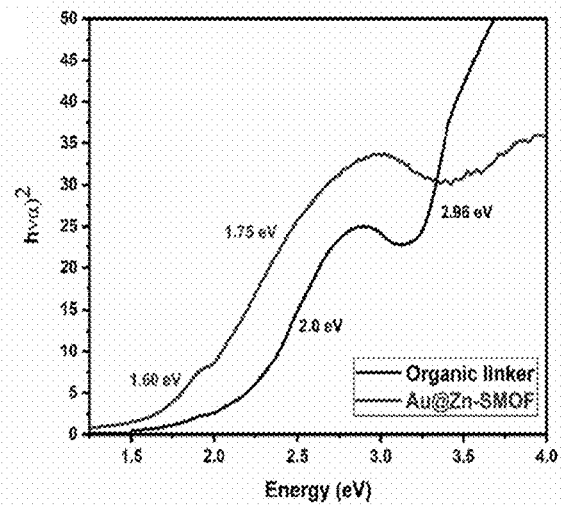
Figure 4C:
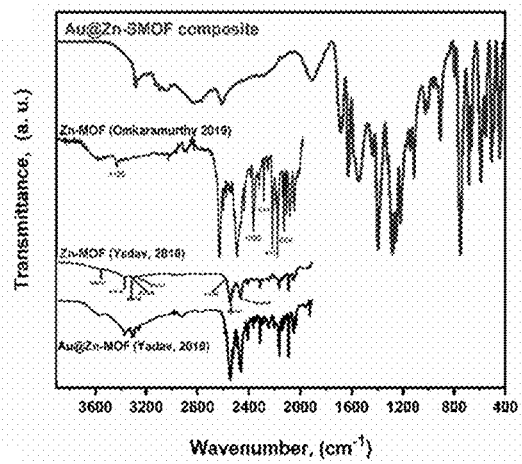

The FT-IR spectrum of Au @Zn-SMOF composite compared with Zn-MOF in published reports [32, 69, 70] was represented in (FIG. 4C). The spectrum shows a peak at 3281 $cm^{-1}$ which was assigned to ($NH_2$) and a weak peak at around 3060 $cm^{-1}$, which was assigned to the aromatic v(C—H) [32, 69]. The bands of 1680, 1626 and 1550 $cm^{-1}$, respectively, were assigned to stretching v(C=O), v(C=N) and v(NH) [32, 69]. The sharp-peaks between 1437 and 1397 $cm^{-1}$ were assigned to v(C=C), the as/symmetric stretching of v(O—C—O) groups, respectively [32, 71-73]. The bands between 1145 and 796 $cm^{-1}$ were assigned to vibrations of d(C—H) and g(C—H) of the aromatic benzene rings v(CH) [71]. The peaks between 749-662 $cm^{-1}$ were assigned in/out of plane bending vibrations of the aromatic-ring [32]. The bands appearing at 507 and 443 $cm^{-1}$ were assigned to coordination and covalent with oxygen and nitrogen v(Zn<-O), v(Zn—N), respectively as evidence of complexation with zinc ion with organic linker. These peaks are not present in organic linker [74].

$^1$H-NMR Spectra

Figure 4D:
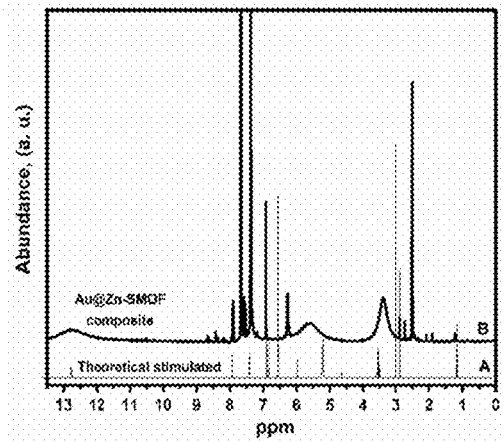

The $^1$H-NMR spectrum of the Au@Zn-SMOF composite is compared with theoretical stimulated spectrum in FIG. 4D. The spectrum showed a signal at 12.65 ppm of OH of carboxylic group node and the signals appearing between 7.93, and 6.7 ppm were assigned to aromatic ring protons. The broad signal at 5.5 ppm was due to amine groups and the signals at 8.13 and 2.9 ppm were assigned to the CHO and $CH_3$ of DMF solvent. The signals at 3.5 and 1.22 ppm were attributed to $CH_2$ and $CH_3$ protons of ethanol [75, 76].

XRD Analysis

Figure 4E:
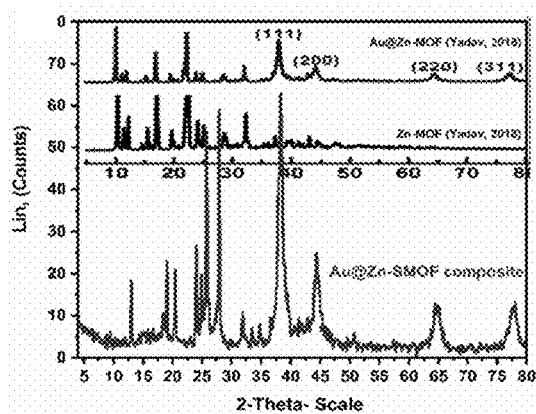

The powder Au@Zn-SMOF composite XRD spectrum compared with Zn-MOF published reports [32, 69, 70, 77] as represented in FIG. 4E. The Au@Zn-SMOF composite XRD patterns showed sharp-peaks which prove that the Au@Zn-SMOF composite crystalline-phase was obtained. Furthermore, the diffraction patterns matched with Zn-MOF-JCPDS no. 18-1486 [69]. The XRD patterns of Au@Zn-SMOF composite shows diffraction peaks at 38.29, 44.46, 64.66 and 77.67 which are the distinctive bands related to the (111), (200), (220), and (311) planes of face-centered-cubic gold-nanoparticles [32, 33].

Thermal Analysis

Figure 4F:
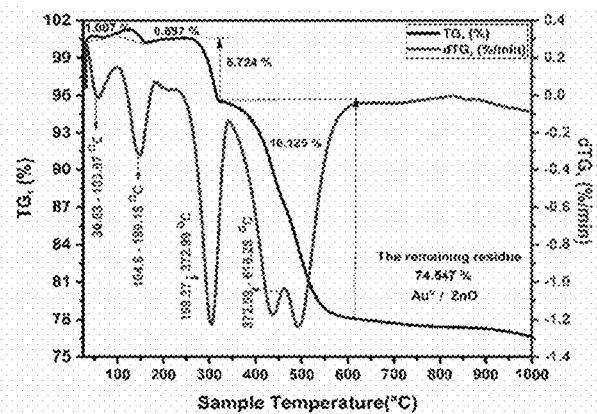

The thermal behavior of Au@Zn-SMOF composite (TGA/dTG) plots (FIG. 4F) compared with Zn-MOF published reports [69, 77]. The Au@Zn-SMOF composite thermogram displays that pass through four points of breakdown are clearly observed. The first point of weight loss (1.005 wt %) in a temperature between 30.83-103.87° C. could be due to the loss of free-lattice ethyl alcohol molecule. The second point of weight loss (0.597 wt %) in a temperature between 104.6-199.15° C. could be due to the loss of inter-lattice water molecule. The third point of weight loss (5.724 wt %) in a temperature between 199.37-372.99° C. could be due to the loss of free-lattice DMF molecules. The last point of weight loss (18.125 wt %) in a temperature between 372.99-616.28° C. could be due to the decomposition of the organic groups within the frame-work. The Au@Zn-SMOF composite was stable at a range of temperatures from 372.99-616.28° C. proving the acceptable chemical stability of the present framework. The residual weight after heating the composite to 997.45° C. was of 74.547 wt %. The crystallinity phases detected by the XRD patterns were due to Au metal and ZnO [69, 77].

Detection of hCG Hormone: Applications and Method Validation

Qualitative Detection of hCG Hormone Via Swab Test Device and Validation

As described above, the detection probe (Au@Zn-SMOF@Ab) was prepared according to references [15, 20, 53-55] with some modifications. After preparation, the cotton swabs were soaked in the detection probe overnight as shown in (FIG. 5A). Subsequently, the swabs were left to dry at R.T., and were then ready to use (FIG. 5B). The detection and validation steps were carried out as follows: The swabs were immersed in vials containing different concentrations of β-hCG-hormone standard (5, 20, 50, 100, 500, 1000 mIU/mL) for about 1 min, then out for about ten min and the results were presented in (FIG. 5C). As shown in FIG. 5C, the swab no. (a) is the control, (b) 5.0 mIU/mL, (c) 20.0 mIU/mL, (d) 50.0 mIU/mL, (e) 100.0 mIU/mL, (f) 500.0 mIU/mL, and (g) 1000.0 mIU/mL. From the figure it can be noted that the color of swabs changed after 10 min to green in the concentration more than 20.0 mIU/mL (FIG. 5C; c:g). Moreover, the green color intensities were directly proportional to the β-hCG concentration, so we can classify the swab test as a semi-qualitative detection test for a positive sample (positive pregnancy samples β-hCG concentration≥20 mIU/mL). On the other hand, in case of the β-hCG concentration of 5.0 mIU/mL no color change is observed (FIG. 5C; b) which can be considered as a negative sample (negative pregnancy samples (β-hCG concentration≤5.0 mIU/mL). The biosensing strategy of the swab test device based on forming of sandwich immunocomplex between antigen/antibody at the surface of gold nanoparticle of the zinc-salen MOF composite via naked eye color change to green.

The applicability of the current swab test in real samples was investigated. A set of 150 real negative and positive pregnancy samples (50 urine, 50 plasma, and 50 serum samples) were checked via swab tests and the results compared with two pregnancy hCG cassette rapid test kits in the market "NOVA-test-Kit [78] and Medicaldisposables.US-Kit [79]." FIG. 5D is an example of the obtained results. As shown in FIG. 5D, a and b represent a positive pregnant case carried out by the present swab test device and pregnancy cassette in market, respectively. Whereas c and d represent a negative pregnant case carried out by the present swab test device and pregnancy cassette in market, respectively. In general, the obtained results prove the extra-high sensitivity of the swab test device with the positive and negative samples in different types of biological samples. The results were confirmed with two different products present in the market [78, 79]. The present swab test offered a higher sensitivity and more accuracy than the two-present product with efficiency reaching to 96±2%.

Figure 6A:
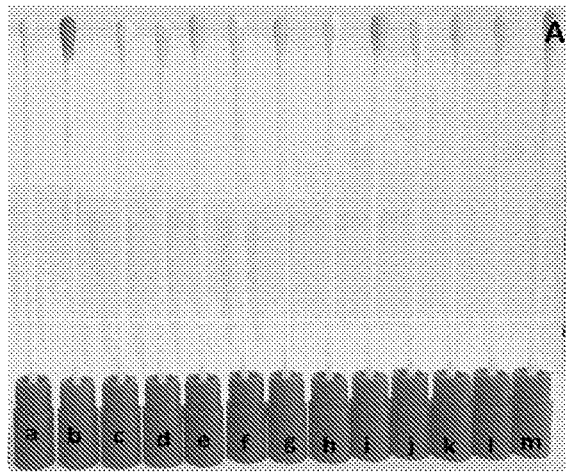
FIGS. 6A-C. (A) A selectivity study for swab test device [Swab no. a, Control; b, β-hCG; c, BSA; d, CEA; e, FSH; f, LH; g, PRL; h, PSA; i, AFP; j, Glu; k, UA; 1, Nat; m, Cl$^-$] (B) The efficacy of swab test device per week (Lifetime of swab), and (C) A smartphone photography image for a group of the swab test devices ready for marketing.
Figure 6B:
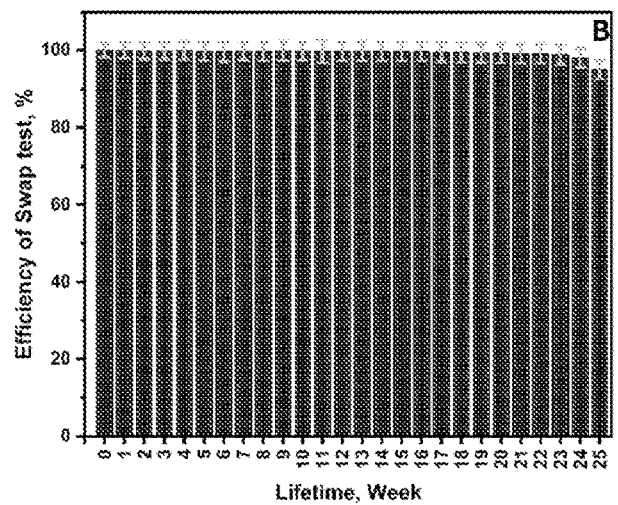
Figure 6C:
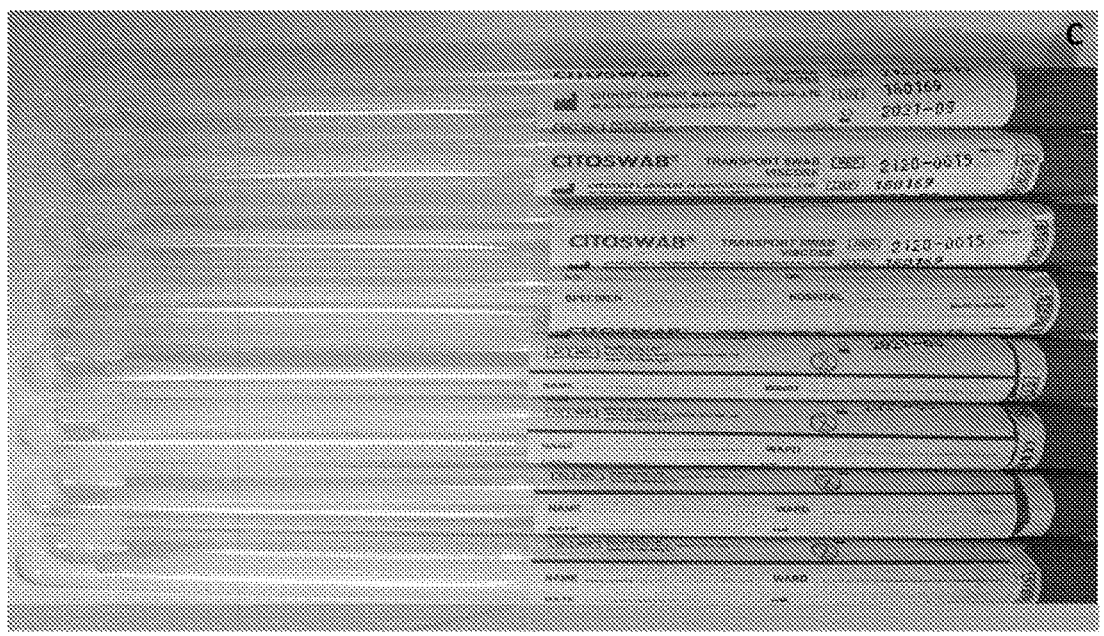

The selectivity and lifetime of the swab test device were also investigated. Firstly, the specificity was evaluated, the performance of swab test device was examined against common hormones, proteins, electrolytes, and organic matrix as represented in FIG. 6A. In this Figure, the swab no. [a] Control; [b] β-hCG 100 mIU/mL; [c] Bovine serum-albumin (BSA) 10 µg/mL; [d] Carcinogenicity-antigen (CEA) 1000 ng/mL; [e] Follicle stimulating hormone (FSH) 1000 ng/mL; [f] Luteinizing hormone (LH) 1000 ng/mL; [j] Prolactin (PRL) 1000 ng/mL; [h] Prostate-specific-antigen (PSA) 1000 ng/mL; [i] α-fetoprotein (AFP) 1000 ng/mL; [j] Glucose (Glu) 500 mg/dL; [k] Uric acid (UA) 100 mg/dL; [l] Sodium ion (Nat) 100 mM; [m] Chloride ion (Cl⁻) 100 mM. FIG. 6A shows a color change to green in case of β-hCG sample, and nothing occurs with other interfering items compared with control swab. These results prove the outstanding specificity for hCG hormone detection. Moreover, the lifetime of the swab test was examined through 25 weeks (approximately six months) as represented in FIG. 6B. The results prove that the swab test device works with high efficiency for this period. Besides the selectivity and lifetime, the accuracy and precision of the swab test immunoassay were evaluated in intra- and inter-assays and during the lifetime evaluation period and the results prove the exceptional accuracy and precision of the swab test. Additionally, the evolution of cost of the present swab test device compared with other devices on the market is lower by about 40%. A smartphone photography image for a group of the swab test device ready for marketing is represented in FIG. 6C. Each swab was inserted into a plastic gap which is ready for use even at home.

Quantitative Detection of hCG Hormone Via Colorimetric Method and Validation

Figure 7A:
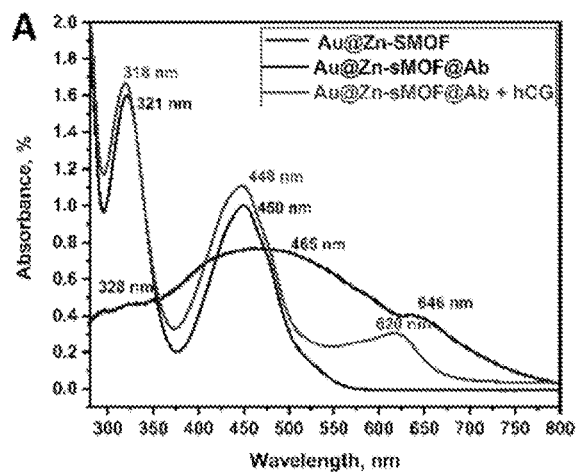
FIGS. 7A-E. (A) The absorption spectra of the Au@Zn-SMOF composite, Au@Zn-SMOF@Ab, and Au@Zn-SMOF@Ab@ β-hCG, (B) The absorption spectra response for behavior of Au@Zn-SMOF@Ab composite towards different concentrations of β-hCG hormone, (C) A dependence calibration curve of the colorimetric immunoassays toward different β-hCG concentrations [Insert in: A Linear relationship (calibration graph) between the absorption intensity and the logarithm β-hCG concentration (log [β-hCG]) at two regions of concentrations], (D) A smartphone photography image for color change with increasing β-hCG concentration, and (E) A histogram of evaluation of the absorption intensity of the Au@Zn-SMOF@Ab towards the β-hCG against different types of interfering analytes [Insert in: The absorption intensity of the Au@Zn-SMOF@Ab towards the β-hCG against different types of interfering analytes].

The absorption spectra of the Au@Zn-SMOF composite, Au@Zn-SMOF@Ab, and Au@Zn-SMOF@Ab@β-hCG were recorded at R.T. and presented in FIG. 7A. From FIG. 7A the Au@Zn-SMOF composite exhibited three UV-Vis absorption peaks at 328, 465, and 646 nm. Whereas the Au@Zn-SMOF@Ab exhibited two UV-Vis absorption peaks at 318 and 448 nm, and we noted that the third band disappeared after conjugation of the antibodies at the surface of gold nano particles, also we noted a red-shift with about 10 nm. However, the Au@Zn-SMOF@Ab@β-hCG exhibited three UV-Vis absorption peaks at 321, 450, and 620 nm. Comparing the absorption spectra of Au@Zn-SMOF@Ab with Au@Zn-SMOF@Ab@β-hCG, we noted a blueshift in the peak with 2-3 nm and a new peak appeared at 620 nm and the color changed from light brown to green. The blueshift in the peaks and new band at 620 nm may be due to the increase of the hydration radius of β-hCG hormone coated with the gold nanoparticles, indicating the formation of detection probe was achieved [15, 20, 53, 54].

Figure 7B:
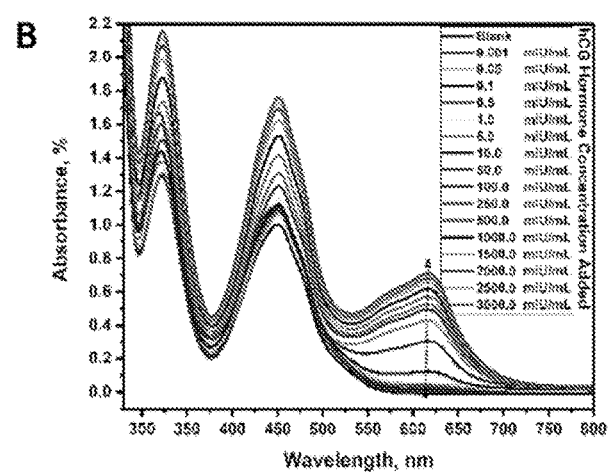
Figure 7C:
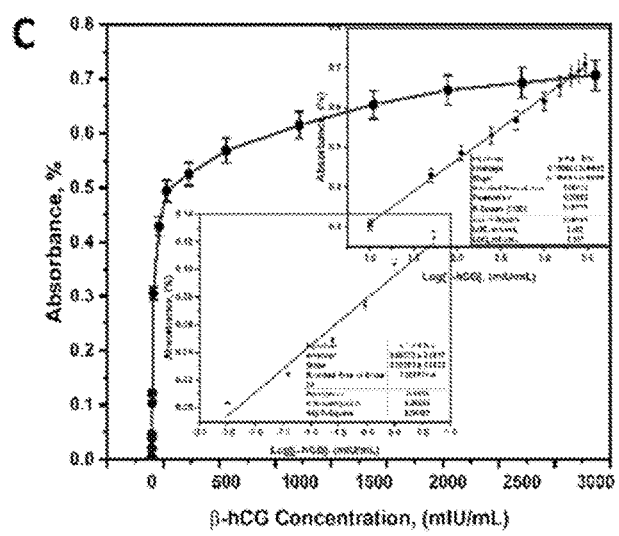

The Au@Zn-SMOF@Ab was examined as a colorimetric biosensor for β-hCG detection and quantification. The absorption spectra of the Au@Zn-SMOF@Ab were investigated against different β-hCG concentrations and the results were represented in FIG. 7B. As shown in FIG. 7B, we can observe an enhancement of the absorption spectra bands with blueshift about 2-3 nm, and a new band at 620 nm. Additionally, by increasing the β-hCG concentration from 0.001 mIU/mL to 3000.0 mIU/mL the absorption intensities gradually increased. Moreover, the colors of the Au@Zn-SMOF@Ab solutions were transformed from the light-brown to green as shown in FIG. 7C. Accordingly, the Au@Zn-SMOF@Ab could be used as naked-eye indicator for β-hCG hormone and colorimetric biosensor.

Figure 7D:
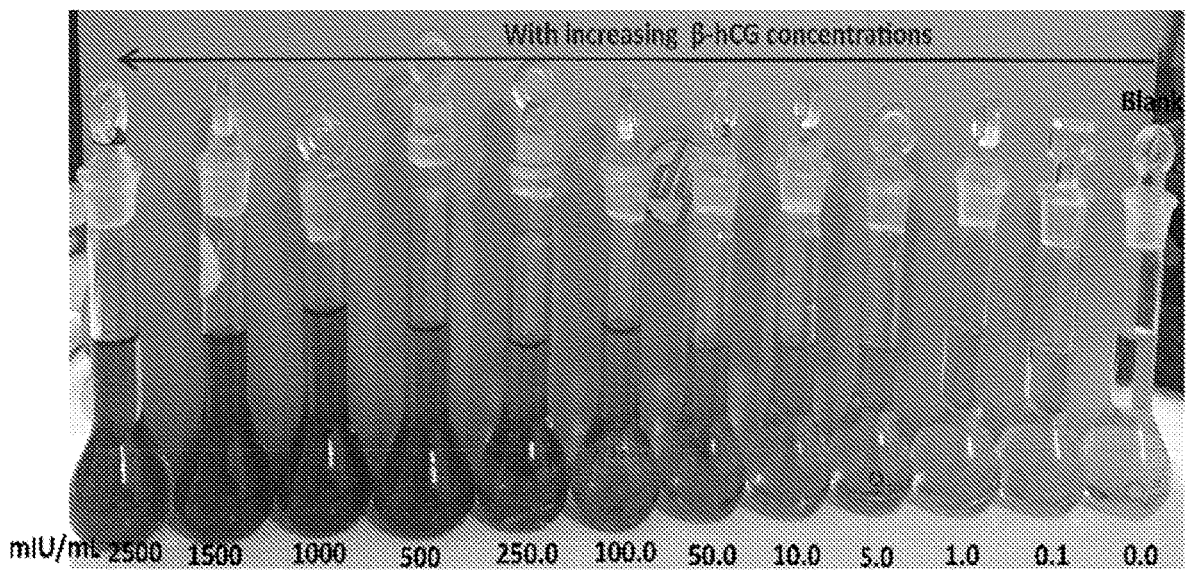

Under the optimal test conditions, as shown in FIG. 7D, a dependence linear relationship was achieved between a series of standard β-hCG phosphate buffered solutions and the absorbance intensities at the three peak areas (321, 450, and 620 nm). For example, at the absorption peak at 620 nm ($Ab_{620}$), the calibration curves of the colorimetric immunoassays showed two β-hCG concentrations regions due to Hook effect; the first region of concentration in a range of (0.001-5.0 mIU/mL), whereas the second region concentration in a range of (10.0-3000.0 mIU/mL). The fitted equations (2) and (3) for the lower and higher concentration ranges (two regions), respectively can be expressed as:

$$\text{Absorbance intensity}(Ab_{620})=0.150+0.159 \text{ Log} \\ [\beta\text{-hCG}] \text{ with } r^2=0.998, \quad (2)$$

$$\text{Absorbance intensity}(Ab_{620})=0.096+0.034 \text{ Log} \\ [\beta\text{-hCG}] \text{ with } r^2=0.991, \quad (3)$$

The colorimetric immunoassay method based on Au@Zn-SMOF@Ab exhibited exceptional sensitivity for hCG detection with lower detection and quantification limits (LOD=0.055 mIU/mL and LOQ=0.167 mIU/mL), comparing with the traditional and previously published reports [1, 3, 4, 7, 14, 15, 17, 22].

Figure 7E:
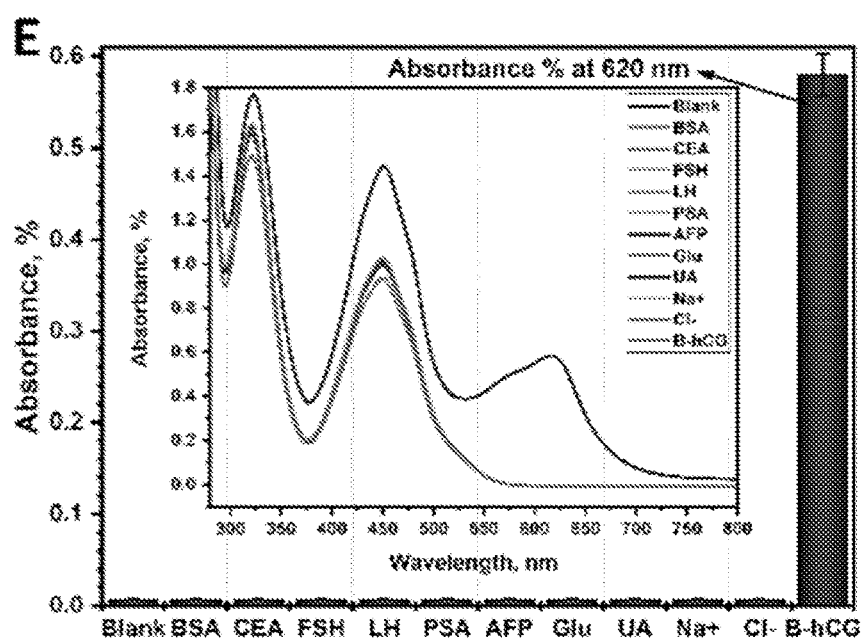

To evaluate the potential specificity and selectivity of Au@Zn-SMOF@Ab towards β-hCG based on current colorimetric immunoassay approaches like in swab test selectivity evolution, the absorption spectra of Au@Zn-SMOF@Ab were examined against different common interfering items like, BSA, CEA, FSH, LH, PSA, AFP, Glu, UA, $Na^+$, and $Cl^-$ and presented in FIG. 7E. As shown in this histogram (Insert in the absorption spectra), the results of the $Abs_{620}$ intensities were extremely enhanced with β-hCG, which doesn't occur with the other interfering matrix which revealed that the Au@ Zn-SMOF@Ab is extremely selective for β-hCG.

The inter- and intra-days accuracy & precision of the present colorimetric immunoassay method were investigated at five concentrations of β-hCG (1.0, 10.0, 100.0, 500.0, and 1500.0 mIU/mL) and each measurement was replicated three times. The $Abs_{620}$ intensities histograms for inter- and intra-days were obtained and the statistical evaluation of data prove the accuracy, precision, reducibility, and repeatability of the present work.

To further evaluate the accuracy of the colorimetric immune-biosensor to quantify the β-hCG concentration content in different real samples (serum/plasma/urine samples), different concentrations of hormone (0.5, 10.0, 100.0, and 1000.0 mIU/mL) were spiked in different real samples and the recovery percent was calculated. The recovery percentage ranged from 98.84% to 100.5% for serum samples; 96.6% to 99.44% for plasma samples; and 96.1% to 97.48 for urine samples. These results prove that the method is applicable, sensitive and effective, for quantification of β-hCG in different real samples.

Mechanism of Biosensing

The investigation of biosensing mechanism and nature of trapping β-hCG hormone was based on the following concepts: (i) The nature of specific and ultra-sensitive recognition between antigen/antibody-immunoassay are keys for detecting this hormone via identification of the change in the detection signals by the basic physiochemical characteristics of the analytes and formation of sandwich-type immunocomplexes [4, 80]. (ii) The distinctive physio-chemical properties of noble metal NPs like Au make it easy to incorporate into dissimilar structures and improve the efficiency of biosensing [32, 81]. (iii) The formation of soft/soft interactions between Au@Zn-SMOF composite and β-hCG or coordination bond with the amino groups in salen-MOF [82, 83]. (iv) The ligand-metal charge transferring (LMCT) effect support the probability of chelation process due to the decreasing of Au @Zn-SMOF composite lipophilicity, and increasing the polarity of the metal ions, so the chelation probability could be increased [84, 85]. So, the biosensing strategy of the swab test device and colorimetric method based on forming of sandwich immunocomplex between antigen/antibody at the surface of gold nanoparticle of the Au@Zn-SMOF@Ab and the high linkage of the Au@Zn-SMOF composite itself leading to naked eye color change to green. The enhancement of the absorbance intensities and the blueshift in present of β-hCG over other competing analytes makes the Au@Zn-SMOF composite an efficient biosensor for directly quantifying and monitoring β-hCG.

CONCLUSION

This work presents a portable swab test device for qualitative detection of β-hCG and a colorimetric approach for quantitative detection. The two analytical tools are based on synthesis of a novel Au@Zn-SMOF composite via a simple and innovative developed method. The evaluation of the swab test device and colorimetric approach demonstrated several advantages over other previously used strip devices and published reports. The swab test device offered a fast, simpler, less expensive, extra-sensitive, and ultra-selective, colorimetric test which is user-friendly and applicable to different types of biological samples (serum/plasma/urine). The colorimetric immunoassay method offered lower detection and quantification limits, more wide linear detection range, and a faster way to quantitate the (3-hCG hormone.

REFERENCES

1. Qu Z, Wang K, Alfranca G, Fuente J M De, Cui D (2020) A plasmonic thermal sensing based portable device for lateral flow assay detection and quantification. Nanoscale Res Lett 15:10 doi.org/10.1186/s11671-019-3240-3
2. Chorionic FUH (2019) False-Negative Urine Human Chorionic Gonadotropin Testing in the Clinical Laboratory. Science (80-) DOI: 10.10:1-8. doi.org/10.1093/labmed/lmz039
3. Qin D, Jiang X, Mo G, Zheng X, Deng B (2020) Electrochemiluminescence immunoassay of human chorionic gonadotropin using silver carbon quantum dots and functionalized polymer nanospheres. Microchim Acta 187:482-
4. Zhang Z, Xu G, Xie L, Guan Y (2019) Colorimetric immunoassay for human chorionic gonadotropin by using peroxidase-mimicking $MnO_2$ nanorods immobilized in microplate wells. Microchim Acta 186:581
5. Tan F, Yan F, Ju H (2007) Sensitive reagentless electrochemical immunosensor based on an ormosil sol-gel membrane for human chorionic gonadotrophin. Biosens Bioelectron 22:2945-2951. doi.org/10.1016/j.bios.2006.12.010
6. Wang Z, Gao Y, Zhang D, Li Y, Luo L, Xu Y (2020) Predictive value of serum β-human chorionic gonadotropin for early pregnancy outcomes. Arch Gynecol Obstet 301:295-302. doi.org/10.1007/s00404-019-05388-2
7. Ajubi N E, Nijholt N (2005) Quantitative automated human chorionic gonadotropin measurement in urine using the Modular Analytics E170 module (Roche). 43:68-70. doi.org/10.1515/CCLM.2005.010
8. Vuong L N, Pham T D, Ho V N A, Ho T M, Humaidan P, Horton M (2020) Determinants of the hCG Concentration in the Early Luteal Phase After Final Maturation of Follicles With Bolus Trigger of Recombinant hCG. Front Endocrinol (Lausanne) 11:1-7. doi.org/10.3389/fendo.2020.00137
9. Grenache D G (2020) Current Practices When Reporting Quantitative Human Chorionic Gonadotropin Test Results. J Appl Lab Med 9:850-857. doi.org/10.1093/jalm/jfaa082
10. Pretorius C J, Toit S, Wilgen U, Klingberg S, Jones M, Ungerer J P J, Tate J R (2019) How comparable are total human chorionic gonadotropin (hCGt) tumour markers assays ? Clin Chem Lab Med doi.org/10.1515/cclm-2019-0457
11. Grenache D G (2020) Progress in understanding the use of human chorionic gonadotropin as a tumor marker. Clin Chem Lab Med 58:323-325
12. Zygmunt M, Herr F, Keller-schoenwetter S, Rao C V, Lang U W E, Preissner K T, Kunzi-rapp K, Mu K, Obstetrics D, Gynecology M Z, Biochemistry KTP, Liebig J (2002) Characterization of Human Chorionic Gonadotropin as a Novel Angiogenic Factor. J Clin Endocrinol Metab 87:5290-5296. doi.org/10.1210/jc.2002-020642

13. Regelson W (1195) Have We Found the "Definitive Cancer Biomarker"? The Diagnostic and Therapeutic Implications of Human Chorionic Gonadotropin-Beta Expression as a Key to Malignancy. Cancer 76:1299-1301
14. Yu S, Sun W, Zhang P, Chen Y, Yan L, Geng L, Yulin D (2020) High Sensitive Visual Protein Detection by Microfluidic Lateral Flow Assay with On-Stripe Multiple Concentration. Chromatographia 83:1145-1151. doi.org/10.1007/s10337-020-03932-w
15. Zhang T, Wang H, Zhong Z, Li C, Chen W, Liu B, Chance B, Photonics B, Bioinformatics H, Imaging M (2020) A smartphone-based rapid quantitative detection platform for lateral flow strip of human chorionic gonadotropin with optimized image algorithm. Microchem J 157:105038. doi.org/10.1016/j.microc.2020.105038
16. Camperi J, Combès A, Fournier T, Pichon V, Delaunay N (2020) Analysis of the human chorionic gonadotropin protein at the intact level by HILIC-MS and comparison with RPLC-MS. 4423-4432
17. Roushani M, Valipour A (2016) Voltammetric immunosensor for human chorionic gonadotropin using a glassy carbon electrode modified with silver nanoparticles and a nanocomposite composed of graphene, chitosan and ionic liquid, and using riboflavin as a redox probe. Microchim Acta 183:845-853. doi.org/10.1007/s00604-015-1731-1
18. Park J, Jung H, Wook Y, Kim H, Kang M, Pyun J (2015) Chemiluminescence lateral flow immunoassay based on Pt nanoparticle with peroxidase activity. Anal Chim Acta 853:360-367. doi.org/10.1016/j.aca.2014.10.011
19. Chen L, Liu B, Liu J, Wan S, Wu T, Yuan J, Member S (2020) Novel Microfiber Sensor and Its Biosensing Application for Detection of hCG Based on a Singlemode-Tapered Hollow Core-Singlemode Fiber Structure. IEEE Sens J 20:9071-9078
20. Guo Y, Zhou Y, Xiong S, Zeng L, Huang X, Leng Y (2020) Natural enzyme-free colorimetric immunoassay for human chorionic gonadotropin detection based on the Ag+-triggered catalytic activity of cetyltrimethylammonium bromide-coated gold nanoparticles. Sensors Actuators B Chem 305:127439 doi.org/10.1016/j.snb.2019.127439
21. Rodrigues J, Pereira S O, Santos N F, Rodrigues C, Costa F M, Monteiro T (2020) Applied Surface Science Insights on luminescence quenching of ZnO tetrapods in the detection of hCG. Appl Surf Sci 527:146813. doi.org/10.1016/j.apsusc.2020.146813
22. Lu W, Chen Z-A, Wei M, Cao X, Sun X (2020) Three-dimensional CoNi-MOF nanosheet array-based immunosensor for sensitive monitoring of human chorionic gonadotropin with core-shell ZnNi-MOF@Nile blue nanotags. Analystst DOI: 10.1039/D0AN01648A. doi.org/10.1039/D0AN01648A
23. Chen P, Sun Q, Xiong F, Zhong H, Yao Z, Zeng Y (2020) A method for the detection of hCG β in spent embryo culture medium based on multicolor fluorescence detection from microfluidic droplets A method for the detection of hCG β in spent embryo culture medium based on multicolor fluorescence detection from mic. Biomicrofluidics 14:024107. doi.org/10.1063/1.5141490
24. Mao X, Ma Y, Zhang A, Zhang L, Zeng L, Liu G (2009) Disposable Nucleic Acid Biosensors Based on Gold Nanoparticle Probes and Lateral Flow Strip. 81:1660-1668
25. Wang H, Ma L, Zhang T, Huang K, Zhao Y (2020) Simple and accurate visual detection of single nucleotide polymorphism based on colloidal gold nucleic acid strip biosensor and primer-specific PCR. Anal Chim Acta 1093:106-114. doi.org/10.1016/j.aca.2019.09.048
26. Sheta S M, El S M, Mohkles S, Elzaher M A, Wassel A R (2019) A novel nano-size lanthanum metal-organic framework based on 5-amino-isophthalic acid and phenylenediamine: Photoluminescence study and sensing applications. Appl Organometal Chem 33:e4777. doi.org/doi. org/10.1002/aoc.4777
27. Sheta S M, El-Sheikh S M, Abd-Elzaher M M (2018) Simple synthesis of novel copper metal-organic framework nanoparticles: Biosensing and biological applications. Dalt Trans 47:4847-4855. doi.org/10.1039/c8dt00371h
28. Liang J, Nuhnen A, Millan S, Breitzke H, Gvilava V, Buntkowsky G, Janiak C (2020) Encapsulation of a Porous Organic Cage into the Pores of a Metal-Organic Framework for Enhanced CO 2 Separation. AngewChemInt Ed 59:6068-6073. doi.org/10.1002/anie.201916002
29. Basaleh A S, Sheta S M (2020) Novel advanced nanomaterial based on ferrous metal-organic framework and its application as chemosensors for mercury in environmental and biological samples. Anal Bioanal Chem 412: 3153-3165
30. Gharib M, Morsali A, Weingart O, Janiak C, Goldman A (2020) Coordinatively unsaturated metal sites (open design and applications †. Chem Soc Rev 2751-2798. doi.org/10.1039/C9CS00609E
31. Toyao T, Saito M, Dohshi S, Mochizuki K, Iwata M, Higashimura H, Horiuchi Y, Matsuoka M (2014) Development of a Ru complex-incorporated MOF photocatalyst for hydrogen production. Chem Commun 50:6779-6781. doi.org/10.1039/c4cc02397h
32. Yadav D K, Gupta R, Ganesan V, Sonkar P K, Yadav M (2018) Gold Nanoparticles Incorporated in a Zinc-Based Metal-Organic Framework as Multifunctional Catalyst for the Oxygen Reduction and Hydrogen Evolution Reactions. ChemElectroChem 5:2612-2619. doi.org/10.1002/celc.201800519
33. Müller M, Turner S, Lebedev O I, Wang Y, Van Tendeloo G, Fischer R A (2011) Au@MOF-5 and Au/MOx@MOF-5 (M=Zn, Ti; X=1, 2): Preparation and microstructural characterisation. Eur J Inorg Chem 5:1876-1887. doi.org/10.1002/ejic.201001297
34. Wu C, Irshad F, Luo M, Zhao Y, Ma X (2019) Ruthenium Complexes Immobilized on an Azolium Based Metal Organic Framework for Highly Efficient Conversion of CO 2 into Formic Acid. ChemCatChem 11:1256-1263. doi.org/10.1002/cctc.201801701
35. Shultz A M, Farha O K, Adhikari D, Sarjeant A A, Hupp J T, Nguyen S T (2011) Selective Surface and Near-Surface Modification of a Noncatenated, Catalytically Active Metal-Organic Framework Material Based on Mn(salen) Struts. Inorg Chem 50:3174-3176
36. Shultz A M, Sarjeant A A, Farha O K, Hupp J T, Nguyen S T (2011) Post-Synthesis Modification of a Metal À Organic Framework To Form. J Am Chem Soc 133:13252 13255. doi.org/10.1021/ja204820d
37. Bhunia A, Lan Y, Powell A K (2011) Salen-based metal-organic frameworks of nickel and the lanthanides. Chem Commun 47:2035-2037. doi.org/10.1039/c0cc04881j
38. Salassa G, Coenen M J J, Wezenberg S J, Hendriksen B L M, Speller S, Elemans J A A W, Kleij A W (2012) Extremely Strong Self-Assembly of a Bimetallic Salen Complex Visualized at the Single-Molecule Level. J Am Chem Soc 134:7186-7192

39. Leoni L, Cort A D (2018) The Supramolecular Attitude of Metal-Salophen and Metal-Salen Complexes. Inorganics 6:42. doi.org/10.3390/inorganics6020042
40. Ashish K. Asatkar, Tripathi M, Deepali A (2019) Salen and Related Ligands. In: Stability and Applications of Coordination Compounds. p DOI: dx.doi.org/10.5772/intechopen.88593
41. Pullen S, Clever G H (2018) Mixed-Ligand Metal-Organic Frameworks and Heteroleptic Coordination Cages as Multifunctional Scaffolds□ A Comparison. Acc Chem Res 51:3052-3064. doi.org/10.1021/acs.accounts.8b00415
42. Wang R, Wu L, Chica B, Gu L, Xu G, Yuan Y (2017) Ni (dmgH) 2 complex coupled with metal-organic frameworks MIL-101 (Cr) for photocatalytic H 2 evolution under visible light irradiation. J Mater 3:58-62. doi.org/10.1016/j.jmat.2016.11.001
43. Leus K, Liu Y, Meledina M, Turner S, Tendeloo G Van, Voort P Van Der (2020) A MoVI grafted Metal Organic Framework: Synthesis, characterization and catalytic investigations. J Catal 316:201-209. doi.org/10.1016/j.jcat.2014.05.019
44. Sheta S M, El-Sheikh S M, Abd-Elzaher M M (2019) A novel optical approach for determination of prolactin based on Pr-MOF nanofibers. Anal Bioanal Chem 411: 1339-1349. doi.org/10.1007/s00216-018-01564-6
45. Sheta S M, El-Sheikh S M, Abd-Elzaher M M, Salem S R, Moussa H A, Mohamed R M, Mkhalid I A (2019) A novel biosensor for early diagnosis of liver cancer cases using smart nano-magnetic metal-organic framework. Appl Organometal Chem 33:e5249. doi.org/10.1002/aoc.5249
46. Tanh Jeazet H B, Janiak C (2014) Metal-Organic Frameworks: Frameworks in Mixed-Matrix Membranes. Encycl Inorg Bioinorg Chem 1-15 doi.org/10.1002/9781119951438.eibc2219
47. Sheta S M, El-sheikh S M, Osman D I, Salem A M, Ali O I, Harraz F A, Shousha W G, Shoeib M A, Shawky S M, Dionysiou D D (2020) A novel HCV electrochemical biosensor based on a polyaniline@Ni-MOF nanocomposite. Dalt Trans 49:8918-8926. doi.org/10.1039/d0dt01408g
48. Go S, Ernst S, Hastu E, Mo M, Aita I El, Wiedey R, Tannert N, NieBing S, Abdpour S, Schmitz A, Quodbach J, Fu G, Henninger S K, Janiak C (2019) Air-Con Metal-Organic Frameworks in Binder Composites for Water Adsorption Heat Transformation Systems. Ind Eng Chem Res 58:21493-21503. doi.org/10.1021/acs.iecr.9b04394
49. Gruber I, Nuhnen A, Lerch A, NieBing S, Klopotowski M, Herbst A, Karg M, Janiak C (2019) Synthesis of Nano/Microsized MIL-101Cr Through Combination of Microwave Heating and Emulsion Technology for Mixed-Matrix Membranes. Front Chem Receiv 7:1-19. doi.org/10.3389/fchem.2019.00777
50. Osman D I, El-sheikh S M, Sheta S M, Ali O I, Salem A M, Gh W, El-khamisy S F, Shawky S M (2019) Nucleic acids biosensors based on metal-organic framework (MOF): Paving the way to clinical laboratory diagnosis. Biosens Bioelectron 141:111451. doi.org/10.1016/j.bios.2019.111451
51. Tahli A, Elshaarawy R F M, Köc Ü, Kautz A C, Janiak C (2016) A HKUST-1 MOF inclusion compound with in-situ reduced copper(I) as [Cu(NCCH<inf>3</inf>)<inf>4</inf>]+ cation complex in the octahedral A-type pore. Polyhedron 117: .doi.org/10.1016/j.poly.2016.06.039
52. Sheta S M, El-Sheikh S M, Abd-Elzaher M M, Ghaneme M L, Salem S R (2019) A novel, fast, high sensitivity biosensor for supporting therapeutic decisions and onset actions for chest pain cases †. RSC Adv 9:20463-20471. doi.org/DOI: 10.1039/c9ra03030a
53. Ni J, Lipert R J, Dawson G B, Porter M D (1999) Immunoassay Readout Method Using Extrinsic Raman Labels Adsorbed on Immunogold Colloids. Anal Chem 71:4903-4908
54. Ma L, Wang H, Zhang T, Xuan Y, Li C, Chen W, Liu B, Chance B, Photonics B, Bioinformatics H, Imaging M (2019) Visual simultaneous detection of single nucleotide polymorphism of tumor susceptibility gene and marker alpha-fetoprotein based on double-labeled colloidal gold probe with lateral flow strip biosensor. Sensors Actuators B Chem 298:126819. doi.org/10.1016/j.snb.2019.126819
55. Ochratoxin A, Juice G, Jiang H, Li X, Xiong Y, Pei K, Nie L, Xiong Y (2017) Silver Nanoparticle-Based Fluorescence-Quenching Lateral Flow Immunoassay for Sensitive Detection of Ochratoxin A in Grape Juice and Wine. Toxins (Basel) 9:83. doi.org/10.3390/toxins9030083
56. Abd-Elzaher M M, Ahmed M A, Farag A B, Attia M, Youssef A O, Sheta S M (2016) Characterization of Eu(III) Complex for Determination of Bumetanide in Pharmaceutical Preparations and in Biological Fluids. Egypt J Chem 59:701-718
57. Abd-Elzaher M M, Ahmed M A, Farag A B, Attia M S, Youssef A O, Sheta S M (2017) A Fast and Simple Method for Determination of Testosterone Hormone in Biological Fluids Based on a New Eu(III) Complex Optical Sensor. Sens Lett 15:977-981. doi.org/10.1166/s1.2017.3904
58. Sheta S M, Akl M A, Saad E, El-gharkawy E R H (2020) A novel cerium(III)-isatin Schiff base complex: spectrofluorometric and DFT studies and application as a kidney biomarker for ultrasensitive detection of human creatinine†. RSC Adv 10:5853-5863. doi.org/10.1039/c9ra10133k
59. Materials R M, Tang J, Man S Q (2013) Green Synthesis of Colloidal Gold by Ethyl Alcohol and NaOH at Normal Temperature. 5372: .doi.org/10.1016/51875-5372(14) 60027-8
60. Pastoriza-santos I, Liz-marza L M (2002) Formation of PVP-Protected Metal Nanoparticles in DMF. 2888-2894
61. Pastoriza-santos BI, Liz-marza LM (2009) FEATURE ARTICLE N, N-Dimethylformamide as a Reaction Medium for Metal Nanoparticle Synthesis. 679-688. doi.org/10.1002/adfm.200801566
62. Das S, Pandey A K, Athawale A A, Subramanian M, Seshagiri T K, Khanna P K, Manchanda V K (2011) Silver nanoparticles embedded polymer sorbent for preconcentration of uranium from bio-aggressive aqueous media. J Hazard Mater 186:2051-2059. doi.org/10.1016/j.jhazmat.2010.12.132
63. Jiang L, Xu S, Zhu J, Zhang J, Zhu J, Chen H (2004) Ultrasonic-Assisted Synthesis of Monodisperse Single-Crystalline Silver Nanoplates and Gold Nanorings. Inorg Chem 43:5877-5883
64. Zhang Z, Chen X, Zhang X, Shi C (2006) Synthesis and magnetic properties of nickel and cobalt nanoparticles obtained in DMF solution. Solid State Commun 139 139:403-405. doi.org/10.1016/j.ssc.2006.06.040
65. Isomura Y, Narushima T, Kawasaki H (2012) Surfactant-free single-nano-sized colloidal Cu nanoparticles for use as an active catalyst in Ullmann-coupling reaction w. Chem Commun 48:3784-3786. doi.org/10.1039/c2cc30975k 66. Hyotanishi M, Isomura Y, Yamamoto H, Kawasaki H (2011) Surfactant-free synthesis of palladium nanoclusters for their use in catalytic cross-coupling reactions w. Chem Commun 47:5750-5752. doi.org/10.1039/c1cc11487e
67. Yamamoto H, Yano H, Kouchi H, Obora Y, Arakawa R, Kawasaki H (2012) N,N-Dimethylformamide-stabilized gold nanoclusters as a catalyst for the reduction of 4-nitrophenol. Nanoscale 4:4148-4154. doi.org/10.1039/c2nr30222e
68. Yao W, Gong W, Li H, Li F (2014) Synthesis of DMF-protected Au NPs with different size distributions and their catalytic performance in the Ullmann homocoupling of aryl iodides. Dalt Trans 43:15752-15759. doi.org/10.1039/c4dt01856g
69. Omkaramurthy B M, Krishnamurthy G (2019) Synthesis, characterization, crystal structure, and electrochemical study of zinc (II) metal-organic framework. Inorg Nano-Metal Chem 49:375-384. doi.org/10.1080/24701556.2019.1661460
70. Sacourbaravi R, Ansari Z, Mohammad A, Valiollah K, Esmaeil N (2020) Fabrication of Ag NPs/Zn-MOF Nanocomposites and Their Application as Antibacterial Agents. J Inorg Organomet Polym Mater. doi.org/10.1007/s10904-020-01601-x
71. Yin D, Li C, Ren H, Shekhah O, Liu J, Liang C (2017) Efficient Pd@MIL-101(Cr) hetero-catalysts for 2-butyne-1,4-diol hydrogenation exhibiting high selectivity. RSC Adv 7:1626-1633. doi.org/10.1039/c6ra25722d
72. Jarrah A, Farhadi S (2018) K6P2W18O62 encapsulated into magnetic Fe3O4/MIL-101 (Cr) metal-organic framework: a novel magnetically recoverable nanoporous adsorbent for ultrafast treatment of aqueous organic pollutants solutions. RSC Adv 8:37976-37992
73. Ezhil Vilian A T, Dinesh B, Muruganantham R, Choe S R, Kang S M, Huh Y S, Han Y K (2017) A screen printed carbon electrode modified with an amino-functionalized metal organic framework of type MIL-101(Cr) and with palladium nanoparticles for voltammetric sensing of nitrite. Microchim Acta 184:4793-4801. doi.org/10.1007/s00604-017-2513-8
74. Kavitha N, Lakshmi P V A (2017) Synthesis, characterization and thermogravimetric analysis of Co (II), Ni (II), Cu (II) and Zn (II) complexes supported by ONNO tetradentate Schiff base ligand derived from hydrazino benzoxazine. J Saudi Chem Soc 21:S457-S466. doi.org/10.1016/j.jscs.2015.01.003
75. Sheta S M, El-sheikh S M, Abd-elzaher M M, Mosaad G L, Salem S R (2019) A novel, fast, high sensitivity biosensor for supporting therapeutic decisions and onset actions for chest pain cases †. RSC Adva 9:20463-20471. doi.org/10.1039/C9RA03030A
76. Sheta S M, Akl M A, Saad H E, El-Gharkawy E S R H (2020) A novel cerium(iii)-isatin Schiff base complex: Spectrofluorometric and DFT studies and application as a kidney biomarker for ultrasensitive detection of human creatinine. RSC Adv 10:5853-5863. doi.org/10.1039/c9ra10133k
77. Sanchez-sanchez IDM (2014) Room temperature synthesis of metal organic framework MOF-2. doi.org/10.1007/s10934-014-9823-6
78. www.invitro-test.com/IVD-reagents/immuno-assay/fertility/hCG-Pregnancy-Rapid-Tests.php, last Accessed October 2020
79. www.medicaldisposables.us/hCG-cassette-pregnancy-test-p/w1-c.htm. last accessed October, 2020.
80. Luo X, Davis J J, Davis J J (2013) Electrical biosensors and the label free detection of protein disease biomarkers. Chem Soc Rev 42:5944-5962 doi.org/10.1039/c3cs60077g
81. Ye Z, Wei L, Xiao L (2019) Chemical Science Laser illumination-induced dramatic catalytic activity change on Au nanospheres † 5793-5800. doi.org/10.1039/c9sc01666j
82. Zhang L, Wang J, Du T, Zhang W, Zhu W, Yang C, Yue T, Sun J, Li T, Wang J (2019) NH2-MIL-53 (Al) Metal-Organic Framework as the Smart Platform for Simultaneous High-Performance Detection and Removal of Hg 2+. Inorg Chem. doi.org/10.1021/acs.inorgchem.9b01242
83. Sheta S M, El-sheikh S M, Abd-elzaher M M (2019) A novel optical approach for determination of prolactin based on Pr-MOF nanofibers. Anal Bioanal Chem 411: 1339-1349
84. Pal S, Bhunia A, Jana P P, Dey S, Möllmer J, Janiak C, Nayek H P (2015) Microporous La-Metal-Organic Framework (MOF) with large surface area. Chem—A Eur J 21:2789-2792. doi.org/10.1002/chem.201405168
85. Wu Y, Wu W, Zou L, Feng J, Gu C, Li B, Batten S R, Yadav R, Kumar A (2016) Luminescent sensing of a new 8-connected topological metal-organic framework. Inorg Chem Commun 70:160-163. doi.org/10.1016/j.inoche.2016.06.007

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A metal organic framework composite, comprising:
a plurality of zinc ions,
a salen ligand, wherein each of said plurality of zinc ions are coordinated with the salen ligand to form a salen complex metal-organic framework; and
gold nanoparticles dispersed on a surface and pores of the salen complex metal-organic framework; wherein the salen ligand is

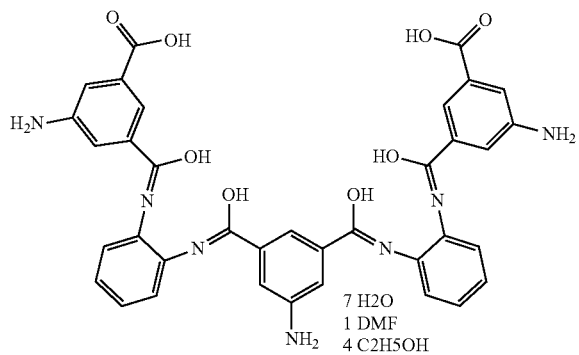 [SMILES: Nc1cc(C(=O)O)cc(C(O)=Nc2ccccc2/N=C(\O)c2cc(N)cc(/C(O)=N/c3ccccc3/N=C(\O)c3cc(N)cc(C(=O)O)c3)c2)c1]

2. The metal organic framework composite of claim 1, wherein the salen complex metal-organic framework forms nanosheets.

3. The metal organic framework composite of claim 2, wherein the nanosheets have a thickness of 100 nm or less.

4. The metal organic framework composite of claim 1, wherein the gold nanoparticles have a diameter of 350-450 nm.

5. The metal organic framework composite of claim 1, further comprising an antibody immobilized on a surface of the gold nanoparticles.

6. The metal organic framework composite of claim 5, wherein the antibody is a β-human chorionic gonadotropin (hCG) monoclonal antibody.

7. A device for detecting a protein biomarker in a biological sample, comprising the metal organic framework composite of claim 5 arranged on a substrate.

8. The device of claim 7, wherein the substrate is a cotton swab.

9. The device of claim 7, wherein the protein biomarker is hCG.

10. A method of detecting a protein biomarker in a biological sample, comprising:
    contacting the biological sample with the metal organic framework composite of claim 5 under conditions suitable for binding the protein biomarker; and
    detecting the protein biomarker by observing a colorimetric change in the solution.

11. The method of claim 10, wherein the protein biomarker is β-hCG.

12. The method of claim 11, wherein the biological sample is selected from the group consisting of serum, plasma, and urine.

13. The method of claim 11, wherein the colorimetric change is from yellow to green.

* * * * *

UNITED STATES PATENT AND TRADEMARK OFFICE
CERTIFICATE OF CORRECTION

PATENT NO. : 10,989,711 B1
APPLICATION NO. : 17/104008
DATED : April 27, 2021
INVENTOR(S) : Mohamed et al.

It is certified that error appears in the above-identified patent and that said Letters Patent is hereby corrected as shown below:

On the Title Page

Item (72) Please correct the residence of the third and fourth inventors as follows:
Said M. El-Sheikh, Cairo (EG)
Sheta M. Sheta, Cairo (EG)

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*